US009642086B1

(12) United States Patent
Poleg et al.

(10) Patent No.: US 9,642,086 B1
(45) Date of Patent: May 2, 2017

(54) METHOD AND SYSTEM FOR REDUCING POWER CONSUMPTION IN NETWORK-CONNECTED MEASUREMENT UNITS USING PREDICTION

(71) Applicants: Yair Poleg, Nes-Harim (IL); Ariel Stern, Lachish (IL)

(72) Inventors: Yair Poleg, Nes-Harim (IL); Ariel Stern, Lachish (IL)

(73) Assignee: Ayyeka Technologies Ltd., Jerusalem (IL)

( * ) Notice: Subject to any disclaimer, the term of this patent is extended or adjusted under 35 U.S.C. 154(b) by 0 days.

(21) Appl. No.: 15/220,439

(22) Filed: Jul. 27, 2016

(30) Foreign Application Priority Data

Nov. 16, 2015 (GB) .................................. 1520160.1

(51) Int. Cl.
| | |
|---|---|
| *G08C 17/00* | (2006.01) |
| *H04W 52/02* | (2009.01) |
| *H04L 29/08* | (2006.01) |
| *H04W 84/18* | (2009.01) |
| *G01N 35/00* | (2006.01) |

(52) U.S. Cl.
CPC ......... *H04W 52/0216* (2013.01); *H04L 67/12* (2013.01); *G01N 2035/0094* (2013.01); *G01N 2035/00881* (2013.01); *H04W 84/18* (2013.01)

(58) Field of Classification Search
None
See application file for complete search history.

(56) References Cited

U.S. PATENT DOCUMENTS

| 2008/0082470 A1* | 4/2008 | Sobhani Tehrani . G06N 99/005 706/21 |
| 2010/0141423 A1 | 6/2010 | Lin |
| 2011/0082596 A1* | 4/2011 | Meagher ............... H02J 13/001 700/291 |

(Continued)

FOREIGN PATENT DOCUMENTS

| CN | 102869079 | 9/2012 |
| WO | WO 2016/028365 | 2/2016 |

OTHER PUBLICATIONS

Great Britain Office Action of Great Britain Application No. GB1520160.1 mailed on May 13, 2016.

*Primary Examiner* — Otis L Thompson, Jr.
(74) *Attorney, Agent, or Firm* — Pearl Cohen Zedek Latzer Baratz LLP

(57) ABSTRACT

A method and a system for determining sampling schemes of a network-connected measurement unit based on time-varying predictability of the measured signals are provided herein. The method may include the following steps: sampling, via a sensor, a metric indicative of a physical property of an infrastructure system, wherein the sampling is carried out over a training period, at an original sampling scheme; determining, based on the training period, in which future time ranges, whether said metric is predictable within a predefined threshold; and adjusting the original sampling scheme, so that the more said metric is predictable in a future time range, the less said future time range is sampled, to yield an updated sampling scheme. In another embodiment, the prediction of the signal may be used to postpone the transmitting of measurements by the local sensor devices whenever the new measurements do not exceed a predefined threshold beyond the predicted values.

20 Claims, 5 Drawing Sheets

(56) References Cited

U.S. PATENT DOCUMENTS

| | | | |
|---|---|---|---|
| 2011/0082597 A1* | 4/2011 | Meagher | H02J 3/38 700/291 |
| 2016/0047679 A1* | 2/2016 | Jernigan | G01D 18/00 702/116 |
| 2016/0164957 A1* | 6/2016 | Leemet | G06Q 30/04 709/203 |
| 2016/0282132 A1* | 9/2016 | Bostick | G01C 21/3415 |

* cited by examiner

METHOD AND SYSTEM FOR REDUCING POWER CONSUMPTION IN NETWORK-CONNECTED MEASUREMENT UNITS USING PREDICTION

CROSS-REFERENCE TO RELATED APPLICATIONS

This application claims priority of Great Britain Patent Application No. GB1520160.1, filed Nov. 16, 2015, which is hereby incorporated by reference.

FIELD OF THE INVENTION

The present invention relates generally to the field of sensor networks, and in particular, such networks that include sensors that transmit measurements via a wireless channel.

BACKGROUND OF THE INVENTION

Many infrastructure systems such as water pipes and drainage systems require measurements of their operation on an ongoing basis. Sensors, of many kinds and types, are being deployed on site in order to measure various metrics and transmit the measurements, usually via a communication network, to a centralized control center, where the data is being analyzed. These sensors are usually energetically autonomous and are equipped with their own power source, which is usually in the form of a battery and therefore has a limited capacity.

Sampling the signal by the sensor and transmitting the data is power consuming and so the sampling scheme can significantly affect the power consumption of the sensors network as a whole. It is also known that some signals have a more predictable behavior in some time range and less predictable behavior in other time ranges.

WIPO Patent Publication number WO 2016/028365 teaches an apparatus for reducing sensor power consumption, in particular, through predictive data measurements by one or more sensors. In one instance, the apparatus may include one or more sensors and a sensor management module coupled with the sensors and configured to cause the sensors to initiate measurements of data indicative of a process in a first data measurement mode, determine a pattern of events comprising the process based on a portion of the measurements collected by the sensors in the first data measurement mode over a time period, and initiate measurements of the data by the one or more sensors in a second data measurement mode. The second data measurement mode may be based on the pattern of events comprising the process. The pattern may indicate a prediction of appearance of events in the process.

However, the aforementioned apparatus is limited for reducing power consumption of sensor where the signal to be sampled is periodic in nature and so is the prediction. Some signal are non-periodic but predictable all the same (a trivial example is a linear function). For these non-periodic signals, the aforementioned apparatus fail.

Therefore, it would be advantageous to provide a method to use knowledge of the predictability of the measured signal over time, in order to reduce the overall power consumption from the power sources upon which these sensors are dependent, irrespective of whether the signal to be sampled is periodic or not.

SUMMARY OF THE INVENTION

According to some embodiments of the present invention, a method and a system for reducing power consumption at a sensing device, are presented herein. The method may include the following steps: sampling, via a sensor, a metric indicative of a physical property of an infrastructure system, wherein the sampling is carried out over a training time span, at an original sampling scheme, wherein the sampling scheme sets forth sampling points indicating times over the time span in which sampling is carried out; determining, based on the training time span, for which of future time spans, whether said metric is predictable within a predefined threshold, wherein a metric is determined predictable by comparing predicted measurements with real measurements at same time slot within the training time span; and adjusting the original sampling scheme, to yield a revised sampling scheme such that a number of sampling points at the revised sampling scheme where said metric is more predictable than a predefined threshold is reduced, and such that a number of sampling points within future time spans where said metric is less predictable than the predefined thresholds is increased According to other embodiments of the present invention, a method and a system for reducing the transmission of data for sensors on a sensors network based on signal prediction are provided herein for reducing power consumption purposes. The method may include the following steps: obtaining, via a sensor, a plurality of measurements indicative of physical properties of an infrastructure system; applying a prediction algorithm, to generate predicted measurements, based on previously obtained measurements; comparing the predicted measurements with currently obtained measurements, to yield a difference measurements; and transmitting the currently obtained measurements only in a case that the difference measurements are beyond a predefined threshold.

These additional, and/or other aspects and/or advantages of the present invention are set forth in the detailed description which follows.

BRIEF DESCRIPTION OF THE DRAWINGS

For a better understanding of the invention and in order to show how it may be implemented, references are made, purely by way of example, to the accompanying drawings in which like numerals designate corresponding elements or sections. In the accompanying drawings.

Figure 1:
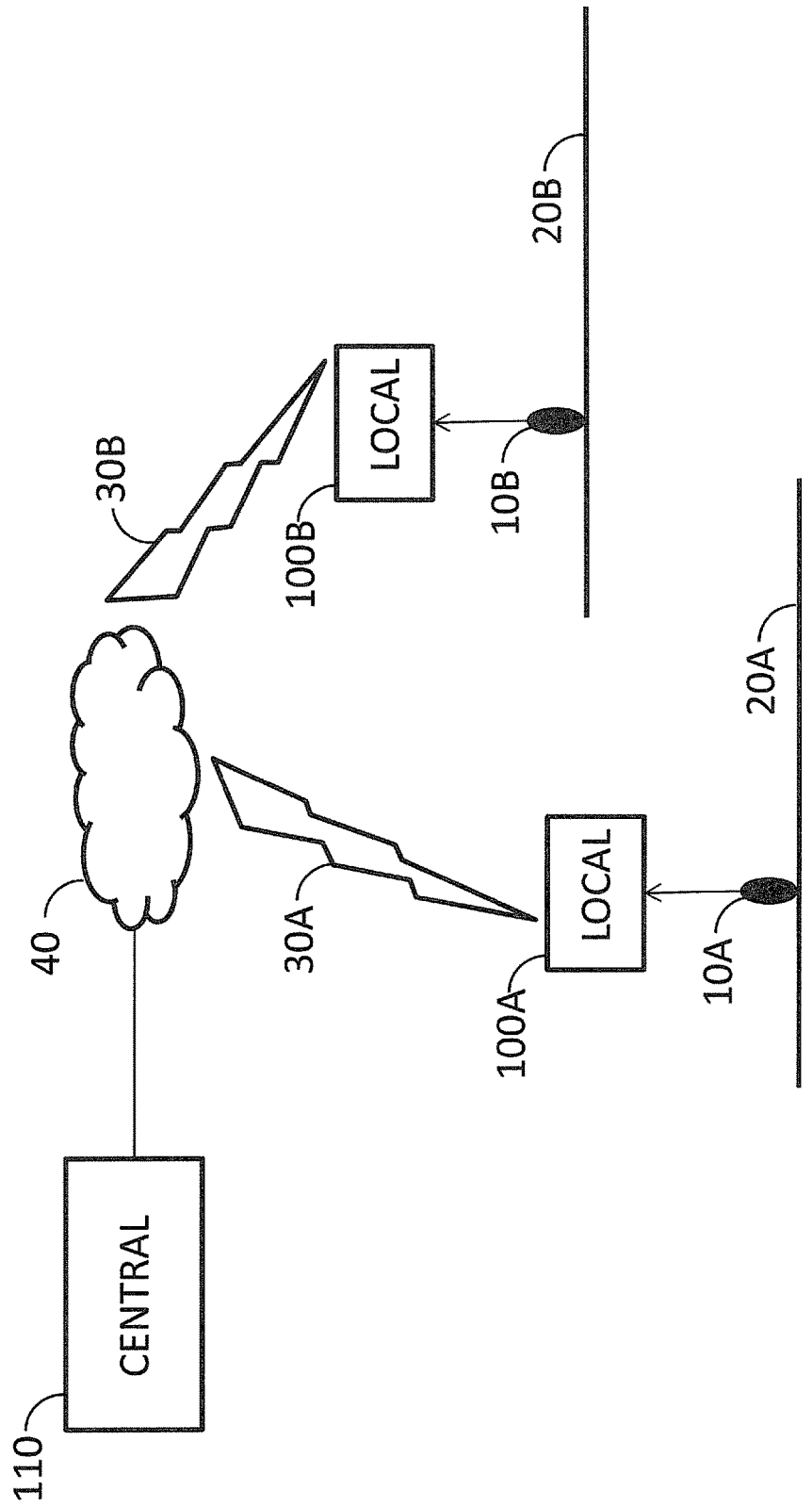
FIG. 1 is a schematic block diagram illustrating the system in accordance with some embodiments of the present invention.

The drawings together with the following detailed description make the embodiments of the invention apparent to those skilled in the art.

DETAILED DESCRIPTION OF THE INVENTION

With specific reference now to the drawings in detail, it is stressed that the particulars shown are for the purpose of example and solely for discussing the preferred embodiments of the present invention, and are presented in the cause of providing what is believed to be the most useful and readily understood description of the principles and conceptual aspects of the invention. In this regard, no attempt is made to show structural details of the invention in more detail than is necessary for a fundamental understanding of the invention. The description taken with the drawings makes apparent to those skilled in the art how the several forms of the invention may be embodied in practice.

Before the embodiments of the invention are explained in detail, it is to be understood that the invention is not limited in its application to the details of construction and the arrangement of the components set forth in the following descriptions or illustrated in the drawings. The invention is applicable to other embodiments and may be practiced or carried out in various ways. Also, it is to be understood that the phraseology and terminology employed herein is for the purpose of description and should not be regarded as limiting.

Predicating data for a specific signal requires some level of prior knowledge of the signal. In extrapolating a signal, known measurements are used to predict the value of the signal in future time slots. In some cases, it is sufficient to 'learn' from the signal itself. In other cases, additional data sources are required. For example: in-pipe pressure levels are mainly affected by day/night changes. Water level in sewage pits is also affected by day/night changes, however, also by the amount rain that drains into the sewage.

The inventors have observed that, in sensors network, in many cases, the data collected by the sensors is highly predictable. This allows, in some embodiments of the present invention, to generate real-valued forecasts. Many prediction algorithms are known in the art, and some embodiments of the present invention may implement the prediction in several non-limiting manners. By way of illustration only, some non-limiting examples for prediction algorithms may include: piecewise linear approximation, polynomial approximation, patch (dictionary) based approximation, and Fourier analysis.

According to some embodiments of the present invention, prediction of the signal can be used to reduce the overall power consumption of the local sensor devices located on site in more than one way. In a first embodiment, the prediction of the signal may be used to postpone the transmitting of measurements by the local sensor devices whenever the new measurements do not exceed a predefined threshold beyond the predicted values. In a second embodiment, the sampling scheme by the local sensing devices is repeatedly adjusted in order to address the nature of the signal based on its predictability. Specifically, the more the signal to be measured is predictable, the less sampling by the local sensing device is required.

In accordance with the first embodiment of the present invention, the forecast could be generated on the server side for power consumption reasons as well as for computational requirements and then sent to the sensing devices. Alternatively, the forecast can be generated by the local sensing device. In both cases, the side that generated the forecast has to share it with the other side.

In the first embodiment, the sensing device receives (or generates) the forecast and monitors in parallel the actual samples of the measured signal. The sensing device will avoid contacting the server as long as the data it collects is close enough to the forecast. When the data deviates from the forecast, the device will transmit all the data it collected to the server. Therefore, this is not a compression algorithm and in any case it's a 'lossless' scheme.

According to the first embodiment of the present invention, a good forecast will allow to postpone the transmission, and therefore extend the battery life by means of reducing the communication overhead. For example, when using a cellular communication network, quite a lot of the energy is being consumed on network registration. This is due to the fact that, in a cellular network, it is required to register to the network, even before transmitting any sensor data. Hence, there is a benefit in transmitting the collected sensor data in large batches. This can be achieved by postponing the communication while accumulating more data to transmit as described above.

FIG. 1 is a schematic block diagram of a system illustrating some embodiments of the present invention. A plurality of local communication devices 100A and 100B, each having its respective sensor 10A and 10B coupled to a respective infrastructure 20A and 20B, are shown. Plurality of local communication devices 100A and 100B are connected over respective wireless channels 30A and 30B to a wireless network 40 and possibly to a central processing unit 110.

Figure 2:
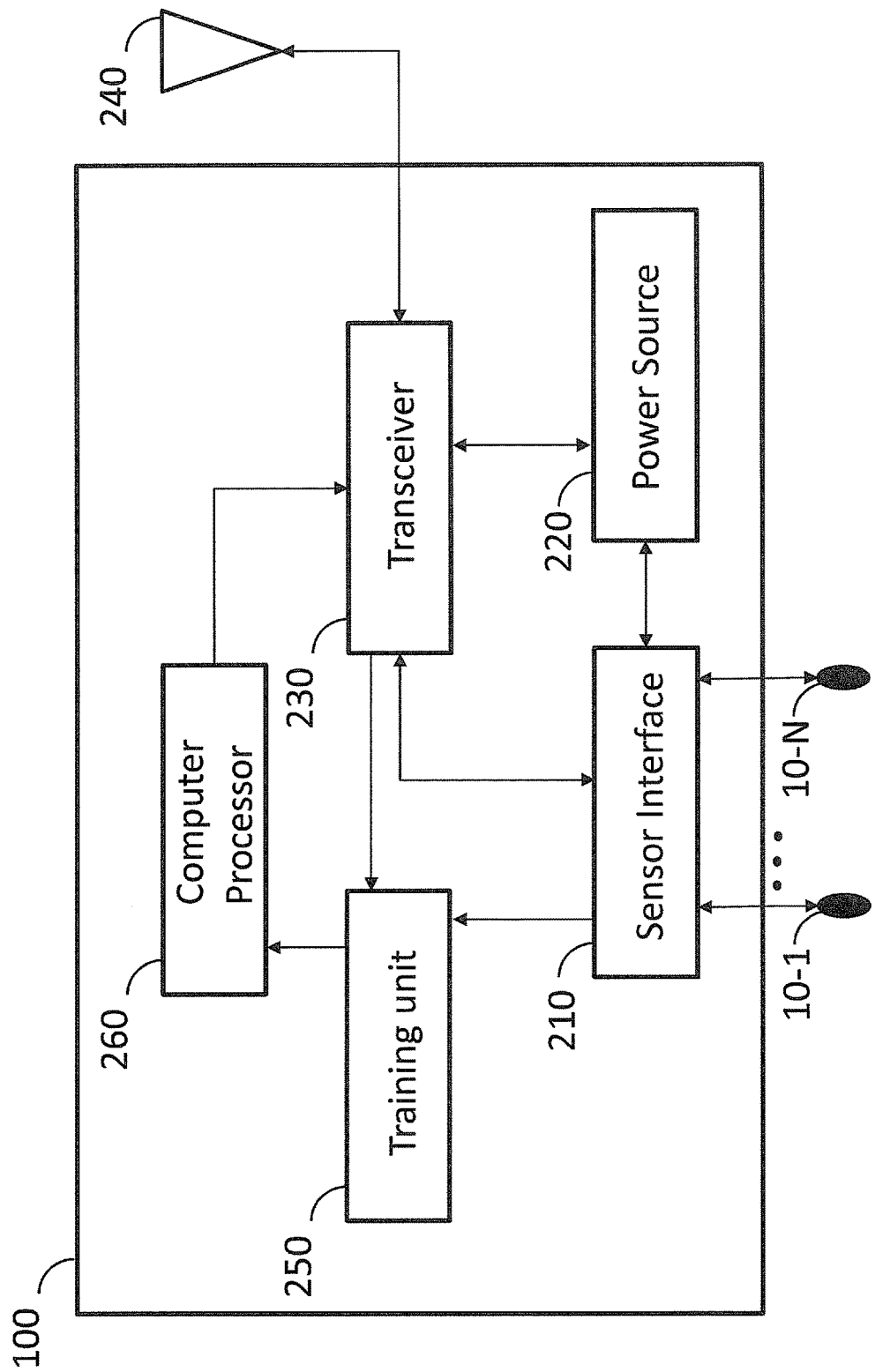
FIG. 2 is a schematic block diagram illustrating in more details the system in accordance with some embodiments of the present invention.

FIG. 2 is an exemplary non-limiting architecture of such a communication device in accordance with some embodiments of the present invention. Exemplary communication device 100 may include a sensor interface 210 configured to be connected to one or more sensors 10-1 to 10-N which in turn are couplable to respective pieces of infrastructure to be measured. Power may be fed by sensor interface 210 to respective sensors 10-1 to 10-N by power source 220. Data collected from sensors 10-1 to 10-N by sensor interface 210 are destined for transmission over the wireless channel by transceiver 230 and antenna 240. Training unit 250 can be used in case signal forecast is generated in the local sensor device and is configured to sample, via a sensor, a metric indicative of a physical property of an infrastructure system, wherein the sampling is carried out over a training period, at an original sampling scheme.

In the first embodiment, the central processing unit (not shown here) applies a prediction algorithm to provide a prediction for next measurements which is conveyed to computer processor 260. The knowledge about the signal is then used by computer processor 260 to compare with actual measurements from sensors 10-1 to 10-N and to decide whether or not to transmit the actual measurement, taking into account power consumption considerations.

In the second embodiment, computer processor 260 (which can be a micro-processor of a field programmable gated array (FPGA)) is then configured to determine, based on the training period, in which future time ranges, whether said metric is predictable within a predefined threshold; and adjusting the original sampling scheme, so that the more said metric is predictable in a future time range, the less said future time range is sampled, to yield an updated sampling scheme.

According to a second embodiment of the present invention, computer processor 260 is further configured to repeat the adjusting of said sampling scheme with updated samples of the updated sampling scheme for further revising the updated scheme.

According to the second embodiment of the present invention, computer processor 260 is further configured to carry out the adjusting of the sampling scheme for achieving a proximal reconstruction of a continuous signal. In other words, if in a specific future range a signal is predictable, so it is not required to sample it just as frequent as before, the measured signal is also reconstructable.

According to some embodiments of the present invention, computer processor 260 is further configured to carry out signal reconstruction by way of at least one of: piecewise linear approximation, polynomial approximation, patch (dictionary) based approximation, and Fourier analysis.

According to the second embodiment of the present invention, computer processor 260 is further configured to determine whether the proximal reconstruction is within a predefined threshold, and in a case it is not, shifting to an alternative sampling scheme based on a specified fallback policy.

According to the second embodiment of the present invention, the aforementioned fall back policy is one of: the original sampling scheme, a subsampling scheme, an over-sampling scheme, and a random sampling scheme. A random scheme may be sometimes advantageous as it may provide important data for signals that tend to behave more predictable in the predefined sampling scheme but rather unpredictable beyond the sampling scheme. Using random sampling has been proved as an effective method for avoiding cases in which periodic sampling scheme fails (e.g., due to lock-stepping).

According to the second embodiment of the present invention, computer processor 260 is further configured calculate the updated sampling scheme for reducing an overall power consumption of the sampling by said sensor.

According to the second embodiment of the present invention, computer processor 260 is further configured to obtain parameters that are external to the sampled metric, and associated with the future time ranges, and wherein the updated sampling scheme is further updated taking into account said external parameters, in reducing the overall power consumption of said sensor.

Figure 3:
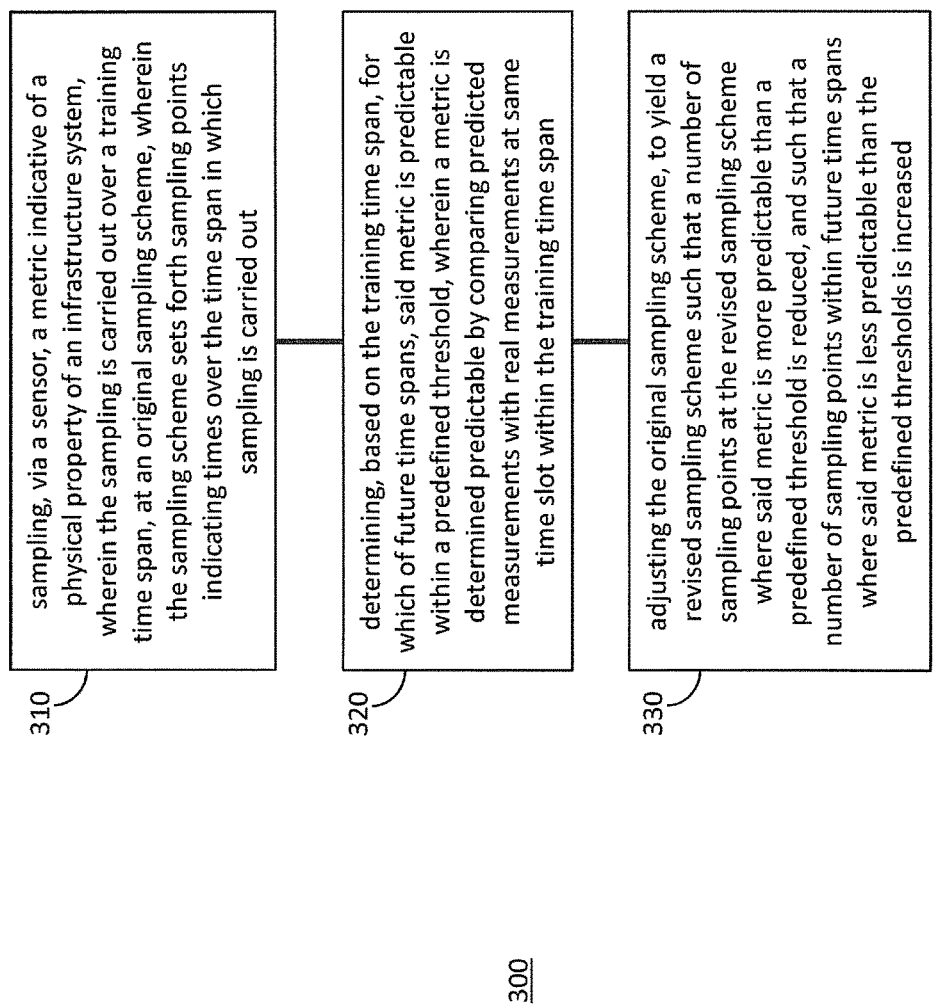
FIG. 3 is a high level flowchart illustrating the method in accordance with some embodiments of the present invention.

FIG. 3 is a flowchart according to the second embodiment of the present invention. Method 300 is a method for determining time varying sampling schemes of a network-connected measurement unit based on measured signal predictability. Method 300 may include the following steps: sampling, via a sensor, a metric indicative of a physical property of an infrastructure system, wherein the sampling is carried out over a training time span, at an original sampling scheme, wherein the sampling scheme sets forth sampling points indicating times over the time span in which sampling is carried out 310; determining, based on the training time span, for which of future time spans, whether said metric is predictable within a predefined threshold, wherein a metric is determined predictable by comparing predicted measurements with real measurements at same time slot within the training time span 320; and adjusting the original sampling scheme, to yield a revised sampling scheme such that a number of sampling points at the revised sampling scheme where said metric is more predictable than a predefined threshold is reduced, and such that a number of sampling points within future time spans where said metric is less predictable than the predefined thresholds is increased 330.

According to the second embodiment, method 300 may also include a step of repeating the adjusting of said sampling scheme with updated samples of the updated sampling scheme for further revising the updated scheme.

According to the second embodiment, the adjusting of the sampling scheme are carried out for achieving a proximal reconstruction of a continuous value defining said metric over time.

According to the second embodiment, method 300 may also include a step of determining whether the proximal reconstruction is within a predefined threshold, and in a case it is not, shifting back to said original sampling scheme and repeating the training period. In some embodiments, the updated sampling scheme is calculated for reducing an overall power consumption of the sampling by said sensor.

According to the second embodiment, method 300 may also include a step of obtaining parameters that are external to the sampled metric, and associated with the future time ranges, and wherein the updated sampling scheme is further updated taking into account said external parameters, in reducing the overall power consumption of said sensor. For example, weather forecast may totally affect the way we plan the sampling because rain may significantly change the flow in sewage pipes.

Figure 4:
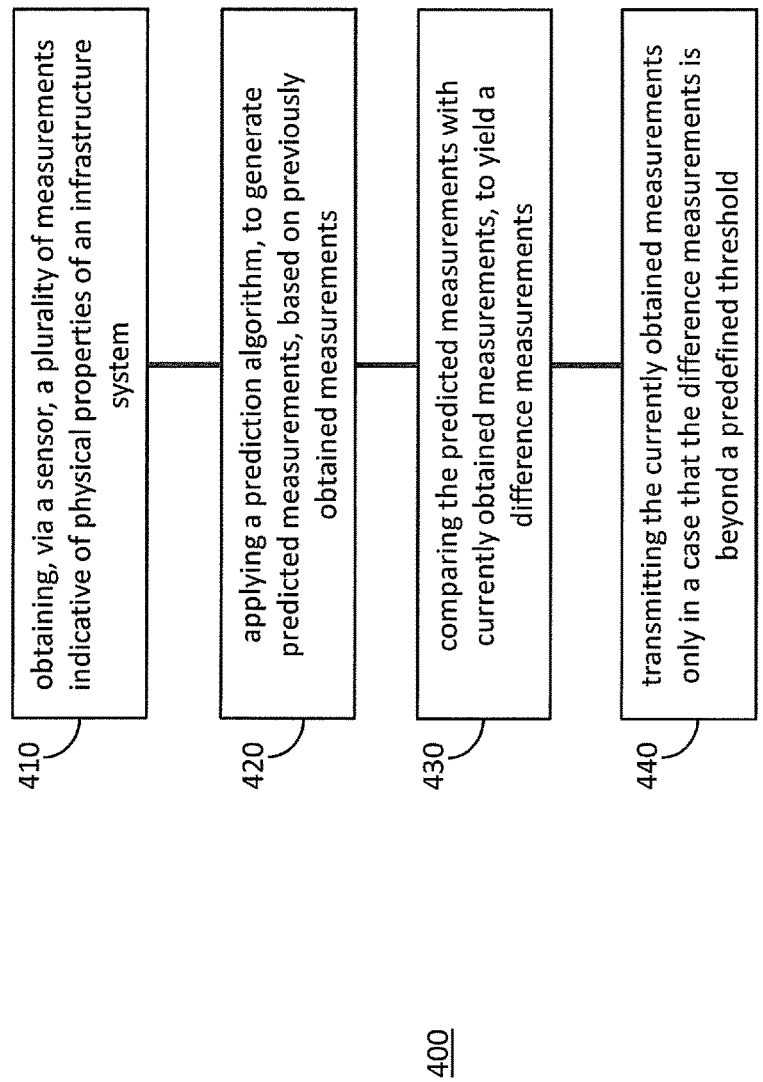
FIG. 4 is a high level flowchart illustrating the method in accordance with other embodiments of the present invention.

FIG. 4 is a flowchart according to the first embodiment of the present invention. Method 400 is a method for reducing data transmission from sensors in a sensors network based on prediction of the measured signal. Method 400 may include the following steps: obtaining, via a sensor, a plurality of measurements indicative of physical properties of an infrastructure system 410; applying a prediction algorithm, to generate predicted measurements, based on previously obtained measurements 420; comparing the predicted measurements with currently obtained measurements, to yield a difference measurements 430; and transmitting the currently obtained measurements only in a case that the difference measurements is beyond a predefined threshold 440.

Figure 5:
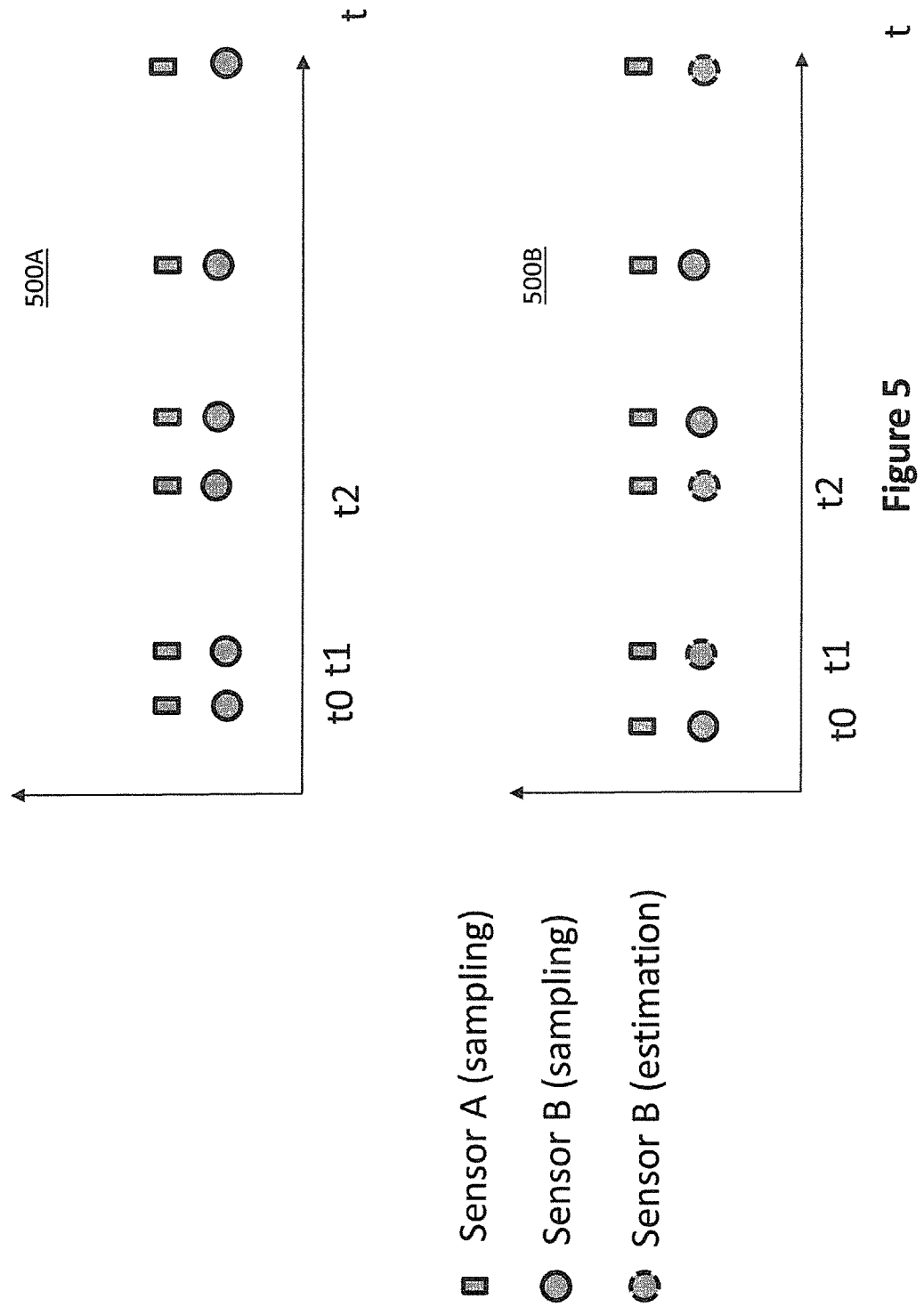
FIG. 5 includes graph diagrams illustrating an aspect in accordance with other embodiments of the present invention.

FIG. 5 includes graph diagrams illustrating an aspect in accordance of some embodiments of the present invention. Graph 500A shows a sampling scheme for two sensors (here sensor A and B) which can be more sensors, sampled in parallel. According to the some embodiments of the present invention, data from sensor A at time t2 can be used, together with previous sampling of sensor B (e.g., time t0 and t1) in order to predict the data that can be sample by sensor B at time t2). Thus, the sampling scheme of sensor B can be changed based on parameters that are external to the sampled metric, which can be a similar metric sampled by a different set of sensors as long as the other metric is dependent is some way or another upon the sampled metric.

Graph 500B shows the modified sampling scheme of sensor B which is sparser. As indicated above this can be achieved only if there is some kind of dependency between the sensors. For example, a sensor configured to check flow in a sewage pipe in one location (sensor B) may be affected by data sampled at a different location on the same sewage network (sensor A).

Additionally and alternatively, the sensors in various location can be used in a collaborated order so as to reduce the amount of sampling and by approximating the sampling using data from dependent sensors as external parameters. Specifically, a given sampling scheme can be carried out by two or more different sensors in different locations in a collaborated manner and taking into account the estimated variations due to the different location. Additionally, any type of dependency between two sensors (or more), whether they are co-located or on different locations, can be used to reduce and make the sampling scheme more compact and more power efficient.

As will be appreciated by one skilled in the art, aspects of the present invention may be embodied as a system, method or an apparatus. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit, "module" or "system."

The aforementioned flowchart and block diagrams illustrate the architecture, functionality, and operation of possible implementations of systems and methods according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

In the above description, an embodiment is an example or implementation of the inventions. The various appearances of "one embodiment," "an embodiment" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "some embodiments", "an embodiment", "one embodiment" or "other embodiments" means that a particular feature, structure, or characteristic described in connection with the embodiments is included in at least some embodiments, but not necessarily all embodiments, of the inventions.

It is understood that, from an implementation point of view, the actual computation such as constructing the graph and solving of the graph may be carried out either on the device, locally, or on the aforementioned central server.

It is to be understood that the phraseology and terminology employed herein is not to be construed as limiting and are for descriptive purpose only.

The principles and uses of the teachings of the present invention may be better understood with reference to the accompanying description, figures and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting" and grammatical variants thereof do not preclude the addition of one or more components, features, steps, or integers or groups thereof and that the terms are to be construed as specifying components, features, steps or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that, where the specification states that a component, feature, structure, or characteristic "may", "might", "can" or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques and procedures for accomplishing a given task including, but not limited to, those manners, means, techniques and procedures either known to, or readily developed from known manners, means, techniques and procedures by practitioners of the art to which the invention belongs.

The descriptions, examples, methods and materials presented in the claims and the specification are not to be construed as limiting but rather as illustrative only.

Meanings of technical and scientific terms used herein are to be commonly understood as by one of ordinary skill in the art to which the invention belongs, unless otherwise defined.

The present invention may be implemented in the testing or practice with methods and materials equivalent or similar to those described herein.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

The invention claimed is:

1. A method for reducing power consumption at a sensing device, the method comprising:

sampling, via a sensor, a metric indicative of a physical property of an infrastructure system, wherein the sampling is carried out over a training time span, at an original sampling scheme, wherein the sampling scheme sets forth sampling points indicating times over the time span in which sampling is carried out;

determining, based on the training time span, for which of future time spans, said metric is predictable within a predefined threshold, wherein a metric is determined predictable by comparing predicted measurements with real measurements at same time slot within the training time span; and adjusting the original sampling scheme, to yield a revised sampling scheme such that a number of sampling points at the revised sampling scheme where said metric is more predictable than a predefined threshold is reduced, and such that a number of sampling points within future time spans where said metric is less predictable than the predefined threshold is increased.

2. The method according to claim 1, further comprising: repeating the adjusting of said sampling scheme with updated samples of the updated sampling scheme for further revising the updated scheme.

3. The method according to claim 1, wherein the adjusting of the sampling scheme is carried out for achieving a proximal reconstruction of a continuous value defining said metric over time.

4. The method according to claim 3, wherein said reconstruction is at least one of: piecewise linear, polynomial approximated, patch based, and Fourier analysis.

5. The method according to claim 3, further comprising: determining whether the proximal reconstruction is within a predefined threshold, and in a case it is not, shifting to an alternative sampling scheme based on a fall back policy.

6. The method according to claim 5, wherein the fall back policy is one of: the original sampling scheme, a subsampling scheme, an oversampling scheme, a random sampling scheme.

7. The method according to claim 1, wherein the updated sampling scheme is calculated for reducing an overall power consumption of the sampling by said sensor.

8. The method according to claim 7, further obtaining parameters that are external to the sampled metric, and associated with the future time ranges, and wherein the updated sampling scheme is further updated taking into account said external parameters, in reducing the overall power consumption of said sensor.

9. The method according to claim 8, wherein the obtaining of the parameters that are external to the sampled metric comprise obtaining measurements from other sensors on the network.

10. A system for reducing power consumption at a sensing device, the system comprising:
a sensor for sensing a metric indicative of a physical property of an infrastructure system, wherein the sampling is carried out over a training time span, at an original sampling scheme, wherein the sampling scheme sets forth sampling points indicating times over the time span in which sampling is carried out;
a computer processor configured to:
determine, based on the training time span, for which of future time spans, said metric is predictable within a predefined threshold, wherein a metric is determined predictable by comparing predicted measurements with real measurements at same time slot within the training time span; and
adjust the original sampling scheme, to yield a revised sampling scheme such that a number of sampling points at the revised sampling scheme where said metric is more predictable than a predefined threshold is reduced, and such that a number of sampling points within future time spans where said metric is less predictable than the predefined thresholds is increased.

11. The system according to claim 10, further comprising: repeating the adjusting of said sampling scheme with updated samples of the updated sampling scheme for further revising the updated scheme.

12. The system according to claim 10, wherein the adjusting of the sampling scheme are carried out for achieving a proximal reconstruction of a continuous value defining said metric over time.

13. The system according to claim 11, further comprising: determining whether the proximal reconstruction is within a predefined threshold, and in a case it is not, shifting to an alternative sampling scheme based on a specified fall back policy.

14. The system according to claim 13, wherein said reconstruction is at least one of: piecewise linear, polynomial approximated, patch based, and Fourier analysis.

15. The system according to claim 13, wherein the fall back policy is one of: the original sampling scheme, a subsampling scheme, an oversampling scheme, a random sampling scheme.

16. The system according to claim 10, wherein the updated sampling scheme is calculated for reducing an overall power consumption of the sampling by said sensor.

17. The system according to claim 10, wherein the computer processor is further configured to obtain parameters that are external to the sampled metric, and associated with the future time ranges, and wherein the updated sampling scheme is further updated taking into account said external parameters, in reducing the overall power consumption of said sensor.

18. The system according to claim 17, wherein the obtaining of the parameters that are external to the sampled metric comprises obtaining measurements from other sensors on the network.

19. A non-transitory computer readable medium comprising a set of instructions that, when executed, cause at least one processor to:
instruct a sensor to sense a metric indicative of a physical property of an infrastructure system, wherein the sampling is carried out over a training time span, at an original sampling scheme, wherein the sampling scheme sets forth sampling points indicating times over the time span in which sampling is carried out;
determine, based on the training time span, for which of future time spans, whether said metric is predictable within a predefined threshold, wherein a metric is determined predictable by comparing predicted measurements with real measurements at same time slot within the training time span; and
adjust the original sampling scheme, to yield a revised sampling scheme such that a number of sampling points at the revised sampling scheme where said metric is more predictable than a predefined threshold is reduced, and such that a number of sampling points within future time spans where said metric is less predictable than the predefined thresholds is increased.

20. The non-transitory computer readable medium according to claim 19, further comprising a set of instructions that when executed cause at least one processor to repeat the adjusting of said sampling scheme with updated samples of the updated sampling scheme for further revising the updated scheme.

* * * * *